United States Patent Office

Re. 25,502
Reissued Dec. 24, 1963

25,502

METHOD FOR THE TREATMENT OF CLONIC TYPE SEIZURES

Edwin J. de Beer, deceased, late of Tuckahoe, N.Y., by Helen I. de Beer, executrix, Tuckahoe, N.Y.; said Edwin J. de Beer assignor to Burroughs Wellcome & Co. (U.S.A.) Inc., Tuckahoe, N.Y., a corporation of New York No Drawing. Original No. 2,955,073, dated Oct. 4, 1960, Ser. No. 738,982, June 2, 1958. Application for reissue Sept. 20, 1962, Ser. No. 225,961
4 Claims. (Cl. 167—65)

Matter enclosed in heavy brackets [ ] appears in the original patent but forms no part of this reissue specification; matter printed in italics indicates the additions made by reissue.

This invention relates to a preparation for the alleviation of *clonic type seizures such as* febrile convulsions.

This condition occurs frequently and is especially a matter of concern in children. In susceptible individuals a rise in body temperature to levels of about 101° F. or somewhat higher is attended by severe convulsive seizures. The convulsive movements may cause bodily injury, severe cardiovascular damage, or even death. It is believed that these febrile convulsions are closely related to epileptic seizures and that a damage resulting from febrile convulsions in childhood predisposes toward epilepsy in later life.

Treatments available at the present time are unsatisfactory, often being inadequate to control the convulsions and difficult to apply. One method frequently used is to cool the patient by means of ice packs. Another method is to place the patient under heavy sedation by means of anesthetic barbiturates until loss of consciousness is approached. Hospitalization is frequently required. Certain anticonvulsants, such as diphenylhydantoin may actually exacerbate the seizures.

The ideal drug for use against febrile convulsions should not only diminish sensitivity to these seizures but should have antipyretic action. Since many barbituric acids derivatives are antipyretics a number of these were examined. Two test procedures were employed. The more fundamentals of these involves a study of the action of drugs against spasms resulting from artificial fever in mice. Since, however, there is experimental correlation between drugs effective against epilepsy and those effective against metrazol-produced spasms, the primary screen was against metrazol spasms.

Method: Experimental seizures were induced in animals by means of pentylenetetrazol (metrazol) and the new compounds were tested for their ability to prevent all seizure activity. Metrazol was employed since the seizures produced are mainly clonic in pattern and drugs effective against such experimental seizures have been found to show some activity clinically in the treatment of petit mal and other minor convulsive disorders.

In the preliminary screening test, doses of 10, 100, and 600 mg./kg. of each drug were administered orally to groups of mice, and anticonvulsant activity was tested at 1, 2, and 3 hours after dosing. Any signs of toxicity, such as depression and incoordination, were noted.

Results: The anticonvulsant potency and toxicity of each new drug was expressed as the percentage of animals protected from the seizure and the percentage showing toxicity, within the dose range of 10 to 600 mg./kg.

Results were as follows:

| B.W. Compound Number | Derivative | Percentage of animals protected against metrazol seizure | Percentage Showing Toxicity |
|---|---|---|---|
| 401 | N-Phenylbarbital | 77 | 33 |
| 413 | N-Phenylneonal | 33 | 67 |
| 402 | N-o-Tolylbarbital | 0 | 33 |
| 403 | N-m-Tolylbarbital | 0 | 50 |
| 404 | N-p-Tolylbarbital | 0 | 0 |
| 407 | N-p-Anisylbarbital | 0 | 19 |
| 409 | N-m-Phenetylbarbital | 0 | 41 |
| 410 | N-p-Phenetylbarbital | 0 | 7 |
| 412 | N-p-Naphthylbarbital | 0 | 19 |
| 473 | N-m-Nitrophenylbarbital | 0 | 13 |
| 489 | N-o-Chlorophenylbarbital | 33 | 40 |
| 56 | N-α-Phenylethylbarbital | 0 | 0 |

These results show that N-phenylbarbital (B.W. No. 401) is unique in this series of N-substituted barbitals, as a compound with marked activity against metrazol-induced clonic seizures.

In further detailed testing, the following results were obtained:

$ED_{50}$—
45 mg./kg. of N-phenylbarbital protected 50 percent of mice from metrazol seizures;
205 mg./kg. protected 50 percent of mice from tonic component of the maximal electroshock seizure.

$TD_{50}$—
170 mg./kg. resulted in mild central nervous system excitability but the depression which occurs with many conventional anticonvulsants was not observed.

The protective index, or ratio of the toxic to the effective dose, of 4.2 was higher than that of phenobarbital, trimethadione, and metharbital, and accordingly indicates a higher degree of safety.

It will be observed that of the above series of barbituric acid derivatives tested, N-phenylbarbital had a unique action different from that of even very close relatives (note Nos. 402–4). Accordingly the more fundamental test procedure was applied to this compound in comparison with drugs of known properties.

Febrile seizures were induced in mice by means of a microwave diathermy generator. In animals between 3 and 4 weeks of age, a generalized seizure response was obtained when the body temperature was raised to 110° F. The threshold convulsive temperature was independent of the rate of temperature rise. The pattern of febrile seizure was principally clonic type. A tonic component observed at higher temperatures was mild, spasmodic, and unsustained. Drugs were tested for their ability (1) to modify the threshold convulsive temperature (2) to abolish the seizure completely and (3) to retard the rate of rise in body temperature in the presence of hyperthermic stimulus.

As shown below, trimethadione, meprobamate and phenobarbital, of value in the treatment of petit mal and myoclonic epilepsies, were effective in the control of febrile seizures, but large and toxic doses were required to abolish the clonus completely. Such drugs are also effective against the clonic metrazol-induced seizure. Diphenylhydantoin, which is ineffective against experimental metrazol seizures, and in petit mal and is used primarily for treatment of tonic major seizures, failed to control the febrile convulsion and indeed, exacerbated the clonic pattern. Acetazolamide raised the threshold convulsive temperature but did not abolish clonus completely; it was also inactive against metrazol-induced seizures.

| Drug | Time of Maximal Effect, hrs. | Fever | | | Metrazol | |
|---|---|---|---|---|---|---|
| | | $ED_{50}$ | $TD_{50}$ | TD/ED | $ED_{50}$ | TD/ED |
| N-Phenylbarbital (B.W. No. 401) | 1½ | 150 | 190 | 1.3 | 45 | 4.2 |
| Phenobarbital | 3 | 103 | 61 | 0.6 | 16 | 3.8 |
| Trimethadione | 1½ | 1,380 | 1,420 | 1.0 | 488 | 2.9 |
| Metharbital | 1½ | 150 | 74 | 0.5 | 40 | 1.9 |
| Diphenylhydantoin | 3 | -------- | 77 | 0 | -------- | 0 |
| Meprobamate | ---------- | 310 | 280 | .9 | -------- | ---------- |

N-phenylbarbital proved remarkably effective against both metrazol and fever-induced seizures. In addition, it was strongly antipyretic and its action was relatively rapid on oral administration. Compared with phenobarbital and metharbital, its toxicity was low and its protective theraupeutic index (ratio of toxic to effective dose) was high.

The compound has the additional advantage of being free from toxic side-effects at doses which effectively protect against febrile convulsions. The side-effects which often may be observed with other compounds may be detected by the following tests: (1) the righting reflex test, (2) the positional sense test, (3) the gait stance test, (4) the muscle tone test, and (5) the equilibrium test. Graded oral doses gave a $TD_{50}$ of 190 mg./kg. for these neural toxicity tests. The lethal action of B.W. 401 required much higher doses. The $LD_{50}$ was found to be 900 mg./kg.

For treatment of febrile convulsions in humans the required dose level is of the order of 3 to 5 mg./kg. three times a day. Roughly, 50–100 mg. in each dose would be given to children and about twice as much to adults. The drug may be presented in capsules, tablets or in the form of an elixir or syrup. The latter is of particular convenience in treating young children.

EXAMPLE 1

Five hundred and thirty g. of N-phenylbarbital is ground thoroughly and sifted through a 60 mesh sieve. It is then mixed with 116.6 g. of dried potato starch and again passed through a 60 mesh sieve. The powder is then granulated twice each time with 80 cc. of 20 percent "Feculose" solution. Feculose is the tradename of a partially degraded starch preparation consisting largely of starch and high-molecular dextrins. The granules are dried overnight at 110° F. and broken up so as to pass through a 24 mesh sieve. To this was added a mixture passed through a 60 mesh sieve of 13.25 g. of dried potato starch and 7.95 g. of stearic acid. The whole was mixed thoroughly and fed into a tabletting machine using No. 74 scored punches. The tablets so prepared weigh 139.5 mg. and contain each 100 mg. of drug.

EXAMPLE 2

Ten g. of N-phenylbarbital is dissolved in 200 cc. of U.S.P. alcohol and to this is added with stirring 200 cc. each of glycerine, propylene glycol and polyethylene glycol 400. A few cc. of lemon extract is then added and the solution is made up to 1 liter with water.

EXAMPLE 3

Ten g. of N-phenylbarbital is dissolved in 350 cc. of U.S.P. alcohol and to this is added 150 cc. of glycerine, 300 cc. of propylene glycol and 100 cc. of 80% cane syrup (U.S.R.). A few cc. of lemon extract are then added and the solution is made up to 1 liter with water.

What I claim is:

1. A method for the treatment of febrile convulsions which comprises the administration of N-phenylbarbital.

2. A method for the treatment of febrile convulsions which comprises the administration of 3–5 mg./kg. of N-phenylbarbital.

*3. A method for the treatment of clonic type seizures which comprises the administration of N-phenylbarbital to a patient suffering from this condition.*

*4. A method as set forth in claim 3, in which the clonic seizure is petit mal.*

References Cited in the file of this patent or the original patent.

Bush: J. Pharmacol., vol. 68, 1940, pp. 278–283 (thru Chem. Abst., vol. 34, 2458).

Hjort: J. Pharmacol., vol. 35, 1929, pp. 155–164 (thru Chem. Abst. 23, 3024).

Cecil: Textbook of Medicine, 7th ed., 1948, p. 28, W. B. Saunders Co.

Cecil: Textbook of Medicine, 9th ed. 1955, pp. 1486–1487.

Williams: Detoxication Mechanisms, 1947, pp. 219–220, John Wiley and Sons, Inc., N.Y.

Irwin: J. Pharm. Exptl. Ther., July 1958, pp. 206–211.

Daly: Staff Meeting Mayo Clinic, May 15, 1957, vol. 32, No. 10, p. 260.